United States Patent [19]

Partis et al.

[11] Patent Number: 5,030,638
[45] Date of Patent: Jul. 9, 1991

[54] METHOD OF ANTIVIRAL ENHANCEMENT

[75] Inventors: Richard A. Partis, Evanston; Richard A. Mueller, Glencoe, both of Ill.

[73] Assignee: G. D. Searle & Co., Skokie, Ill.

[21] Appl. No.: 554,494

[22] Filed: Jul. 19, 1990

Related U.S. Application Data

[62] Division of Ser. No. 484,290, Feb. 26, 1990, abandoned.

[51] Int. Cl.$^5$ ............................................. A61K 31/445
[52] U.S. Cl. ................................................. 514/315
[58] Field of Search ......................................... 514/315

[56] References Cited

U.S. PATENT DOCUMENTS

| | | | |
|---|---|---|---|
| 4,220,782 | 9/1980 | Stoltefuss | 546/242 |
| 4,639,436 | 1/1987 | Junge et al. | 546/242 |
| 4,849,430 | 7/1989 | Fleet et al. | 514/315 |
| 4,871,747 | 10/1989 | Kinast et al. | 514/315 |

FOREIGN PATENT DOCUMENTS

| | | |
|---|---|---|
| 315017 | 5/1989 | European Pat. Off. |
| 87/03903 | 7/1987 | World Int. Prop. O. |

OTHER PUBLICATIONS

Yoshikuni, Y., "Inhibition of Intestinal α-Glucosidase Activity and Postprandial Hyperglycemia by Moranoline and its N-alkyl Derivatives", *Agric. Biol. Chem.*, 52 (1) 121-128, 1988.

Sunkara et al., Biochem. Biophys. Res. Commun. 148, 206-210 (1987).
Tyms et al., Lancet, Oct. 31, 1987, pp. 1025-1026.
Walker et al., Proc. Natl. Acad. Sci. 84, 8120-8124 (1987).
Gruters et al., Nature 330, 74-77 (1987).
Fleet, FEBS Lett. 237, 128-132 (1988).
Fleet et al., Tetrahedron Lett. 26, 3127-3130 (1985).
Fleet et al., Chem. Lett. 1051-1054 (1986).
Karpas et al., Proc. Natl. Acad. Sci. USA 85, 9229-9233 (1988).
Sonigo et al., Cell 42, 369-382 (1985).
Haase, Nature 322, 130-136 (1986).
Frank et al., Antimicrob. Agents & Chemother. 32, 1369-1374 (1987).
Hettkamp, Eur. J. Biochem. 142, 85-90 (1984).
Schweden et al., Arch. Biochem. Biophys. 248, 335-340 (1986).

*Primary Examiner*—Mary C. Lee
*Assistant Examiner*—Lenora A. Miltenberger
*Attorney, Agent, or Firm*—Scott J. Meyer; James W. Williams, Jr.

[57] ABSTRACT

A method for providing enhanced antiviral activity with N-alkyl derivatives of 1,5-dideoxy-1,5-imino-D-glucitol is disclosed which comprises selectively increasing the alkyl chain length to at least 5 carbon atoms and up to about 10 carbon atoms to thereby improve the spectrum of enzyme inhibitory activity and the in vivo half life.

2 Claims, No Drawings

METHOD OF ANTIVIRAL ENHANCEMENT

This is a division of application Ser. No. 484,290, filed Feb. 26, 1990, now abandoned.

BACKGROUND OF THE INVENTION

This invention relates to a method of inhibiting retroviruses such as human immunodeficiency virus (HIV). More particularly, the invention concerns a method for providing enhanced antiviral activity with N-alkyl derivatives of 1,5-dideoxy-1,5-imino-D-glucitol (deoxynojirimycin) which have potential use for the treatment of acquired immune deficiency syndrome (AIDS) and AIDS-related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4$^{30}$ T-cells (or CD4$^{30}$ cells) See, e.g., Gallo et al., *Science* 224, 500–503 (1984), and Popovic et al., *Ibid.*, 224, 497–500 (1984). This retrovirus had been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his coworkers in 1986 [*Nature* 326, 662 (1987)]. As used herein these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

More recently, certain glycosidase inhibitors have been tested for activity against the AIDS virus. Three such compounds suggested as potential anti-AIDS drugs are castanospermine, 1-deoxynojirimycin (DNJ) and 2,5-dihydroxymethyl-3,4-dihydroxy-pyrrolidine (DMDP). See, e.g., Sunkara et al., *Biochem. Biophys. Res. Commun.* 148(1), 206–210 (1987); Tyms et al., *Lancet*, Oct. 31, 1987, pp. 1025–1026; Walker et al., *Proc. Natl. Acad. Sci. USA* 84, 8120–8124(1987);

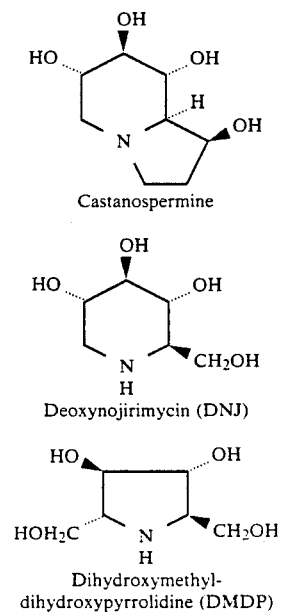

Castanospermine

Deoxynojirimycin (DNJ)

Dihydroxymethyl-dihydroxypyrrolidine (DMDP)

Thus, castanospermine, which is an alkaloid isolated from the seeds of the Australian chestnut tree, has been found to interfere with normal glycosylation of HIV virions, thereby altering the envelope glycoprotein and preventing entry of HIV into target cells. However, only a modest reduction in virion infectivity was found.

In PCT Inter. Appln. WO 87/03903, published July 2, 1987, the N-methyl derivative of deoxynojirimycin (DNJ) also was disclosed as having activity against HIV ostensibly based on its glucosidase I inhibitory activity. However, it was subsequently shown by Fleet et al., *FEBS Lett.* 237, 128–132 (1988), that not all glucosidase I inhibitors are effective inhibitors of HIV. Therefore, some other mechanism may be responsible for HIV inhibitory activity. For example, while the known inhibition of the cytopathic effect (CPE) by the o-glucosidase I inhibitor castanospermine is confirmed, neither the epimer L-1,6-diepicastanospermine nor the stereoisomer of castanospermine, L-6-epicastanospermine, were found to be inhibitory.

So also, although both enantiomers of 1,4-dideoxy-1,4-imino-arabinitol are known glucosidase inhibitors [Fleet et al., *Tetrahedron Lett.* 26, 3127–3130 (1985); Fleet et al., *Chemistry Lett.*, 1051–1054 (1986)], the L-enantiomer has strong HIV inhibitory activity whereas the D-enantiomer has very little effect on HIV replication. For both enantiomers, N-methylation reduced rather than increased anti-HIV activity. Neither the azofuranose analog of glucose nor the N-benzyl derivative were found to have an effect on CPE. Similarly, no HIV inhibition was observed for fagomine, the 2-deoxy-glucose analog, although it too is known to have α-glycosidase inhibitory activity. See Fleet et al., *FEBS Lett.* 237, 128–132 (1988).

Karpas, et al., *Proc. Natl. Acad. Sci. USA* 85, 9229–9233 (1988), report that whereas the N-methyl- and N-ethyl-DNJ reduce the yield of infectious HIV by an order of four and three logarithms, respectively, the N-butyl-DNJ reduces infectious viral particles by a logarithmic order greater than five at nontoxic concentrations. See also U.S. Pat. No. 4,849,430 on the antiviral use of N-butyl-DNJ.

BRIEF DESCRIPTION OF THE INVENTION

In accordance with the present invention a method is provided for providing enhanced antiviral activity with N-alkyl derivatives of 1,5-dideoxy-1, 5-imino-D-glucitol (deoxynojirimycin or DNJ). Although the lower alkyl derivatives of DNJ such as the N-methyl- and N-butyl-DNJ have been reported to have significant antiviral activity, it has been surprisingly found that an enhanced spectrum of glucosidase enzyme inhibitory activity can be obtained in these derivatives by selectively increasing the alkyl chain length to at least 5 carbon atoms and up to about 10 carbon atoms. These higher N-alkyl derivatives of DNJ also have a longer in vivo half life than the lower $C_1$-$C_4$ N-alkyl derivatives.

The enhanced spectrum of enzyme inhibitory activity of these higher N-alkyl derivatives of DNJ compared to the lower $C_1$-$C_4$ N-alkyl derivatives is demonstrated against yeast α-glucosidase at physiologic pH 7.4, and against almond β-glucosidase at physiologic pH 7.4 and at the optimum enzyme activity pH 4.8. This is shown dramatically by the ratio of $IC_{50}$ values. The responsible factors appear to provide for a non-linear relationship with respect to beta-glucosidase inhibition. That is, there is a very sharp decrease in $IC_{50}$ starting at the chain length of $C_5$ in which the potency increases by a factor of 10 over $C_4$. Inhibition of alpha-glucosidase varies by a factor of about 4 over the series with the exception of the $C_1$ compound.

In preliminary pharmacokinetic tests, the illustrative N-nonyl-DNJ surprisingly exhibited a half-life of 5 times that of the N-butyl-DNJ when administered in vivo in rats. That is, the N-nonyl-DNJ has a t½ in vivo in the rat of 6.24 hours when measured as total radioactivity in the blood compared to the t½ of N-butyl-DNJ which is only 1.24 hours. The longer half-life allows less frequent dosing of the mammal to maintain effective blood concentrations of the antiviral agent and prevents wide variations in blood levels. Less frequent drug administration should also reduce the gastrointestinal side effects seen with N-butyl-DNJ. Although the inventors are not to be bound by theory, it is believed that the increase in half-life may be partially due to increased lipophilicity and to increased chain length. Increased lipophilicity should allow increased penetration of the cell membrane and thus provide a higher intercellular concentration relative to surrounding body fluids.

The N-nonyl-DNJ also was found to be metabolized whereas the N-butyl-DNJ was not metabolized as determined by assay for excretion of metabolites in urine of rats. These tests suggest potential use of the higher N-alkyl derivatives of DNJ as longer acting antiviral drugs.

Also in standard in vitro tests, the N-hexyl-DNJ and the N-nonyl-DNJ were demonstrated to inhibit HIV-1. These tests involved plating of susceptible human host cells which are syncytium-sensitive with and without virus in microculture plates, adding various concentrations of the test compound, incubating the plates for 9 days (during which time infected, non-drug treated control cells are largely or totally destroyed by the virus), and then determining the number of remaining viable cells using a colorimetric endpoint.

Potential use against the AIDS virus also is shown by the inhibitory activity of the higher N-alkyl derivatives of DNJ against visna virus in a conventional plaque reduction assay. Visna virus, a lentivirus genetically very similar to the AIDS virus, is pathogenic for sheep and goats. See Sonigo et al., *Cell* 42, 369–382 (1985); Haase, *Nature* 322, 130–136 (1986). Inhibition of visna virus replication in vitro as a useful model for human immunodeficiency virus (HIV) and its inhibition by test compounds has been described by Frank et al., *Antimicrobial Agents and Chemotherapy* 31(9), 1369–1374 (1987).

These results with the higher N-alkyl derivatives of DNJ were unexpected in view of the following two prior reports:

Hettkamp et al., *Eur. J. Biochem.* 142, 85–90 (1984), report that N-dodecyl-1-deoxynojirimycin affects both trimming glucosidases I and II to a lesser degree than deoxynojirimycin or N-methyl-deoxynojirimycin.

In a study of inhibition of glucosidase I by deoxynojirimycin, deoxymannojirimycin and several N-alkyl derivatives, the N-hexyl- and N-decyl-derivatives are reported to have greater $K_i$ values than the N-methyl- and N-butyl-derivatives by Schweden et al., *Arch. Biochem. Biophys.* 248(1), 335–340 (1986).

The higher N-alkyl derivatives of deoxynojirimycin used in the method of the invention have the following chemical structure:

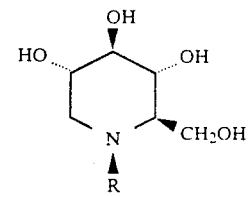

wherein R = $C_{5-10}$ alkyl.

In order to indicate stereoisomerism, solid and dotted lines show bonds directed above or below, respectively, the plane of the paper.

DETAILED DESCRIPTION OF THE INVENTION

The higher N-alkyl derivatives of deoxynojirimycin used in the method of the present invention are known compounds, except for the N-nonyl-DNJ which is believed to be a novel compound. Methods of their preparation and their prior known use as antidiabetic and similar such therapeutic agents are described in U.S. Pat. No. 4,639,436. Thus, they can readily be prepared by reacting 1,5-dideoxy-1,5-imino-D-glucitol (deoxynojirimycin) with an appropriate alkylaldehyde in the presence of a hydrogen donor reducing agent, for example, catalytically activated hydrogen. Hydrogenation in the presence of a noble metal catalyst, for example palladium, at elevated temperature and pressure in methanol solvent medium is suitable. Appropriate alkylaldehydes for preparing the corresponding $C_5$ to $C_{10}$ N-alkyl derivatives are, for example, n-pentanal, n-hexanal, n-heptanal, n-octanal, n-nonanal, and n-decanol, respectively. It will be appreciated, however, that the method of the invention is not limited to any particular method of preparation of the N-alkyl-DNJ.

The following examples will further illustrate the invention in greater detail although it will be understood that the invention is not limited to these specific examples or the details therein. Examples 1 to 3 illustrate the preparation of N-pentyl-, N-hexyl- and N-nonyl derivatives of 1,5-dideoxy-1,5-imino-D-glucitol (deoxynojirimycin) by the reaction of deoxynojirimycin with appropriate alkylaldehyde accompanied by catalytic hydrogenation. Example 4 illustrates the preparation of the N-tetradecyl derivative of DNJ which was used for comparative purposes. Example 5 illustrates the effect of these compounds when tested for inhibition of visna virus in vitro in a plaque reduction assay. Example 6 illustrates the enzyme inhibitory activity of these compounds when tested in vitro (A) against almond $\beta$-glucosidase, both at about physiologic pH 7.4 and the optimum enzyme activity pH 4.8, and (B) against yeast $\alpha$-glucosidase at pH 7.4. Example 7 illustrates the effect of the preferred N-hexyl- and N-nonyl-DNJ compounds against HIV in an in vitro cell culture test.

EXAMPLE 1

1,5-(Pentylimino)-1,5-dideoxy-D-glucitol

A solution of 1,5-dideoxy-1,5-imino-D-glucitol (0.64 g, 0.0039 mole), valeraldehyde (0.40 g, 0.0047 mole), and 5% Pd black (0.1 g) in methanol (30 ml) was hydrogenated (5 psi/25° C./89 hrs.). After filtering the resulting mixture, the filtrate was concentrated on a rotary evaporator to an oil. Chromatography on silica gel followed by crystallization from acetone gave the title compound, m.p. ca. 103° C. Structure assignment was supported by NMR, infrared spectra and elemental analysis. (233.31).

Analysis calcd. for $C_{11}H_{23}NO_4$: C, 56.63; H, 9.94; N, 6.00. Found: C, 56.55; H, 9.75; N, 6.03.

EXAMPLE 2

1,5-(Hexylimino)-1,5-dideoxy-D-glucitol

A solution of 1,5-dideoxy-1,5-imino-D-glucitol (0.5 g, 0.0031 mole), caproaldehyde (0.45 g, 0.0045 mole) and 5% Pd black (0.1 g) in methanol (105 ml) was hydrogenated (5 psi/25° C./5 days). After filtering the resulting mixture, the filtrate was concentrated with a flow of nitrogen to give an oily solid. The title compound was crystallized and recrystallized from acetone-ethanol, DSC ca. 115° C. Structural assignment was supported by NMR, infrared spectra and elemental analysis (247.3).

Analysis calcd. for $C_{12}H_{25}NO_4$: C, 58.27; H, 10.19; N, 5.66.

Found: C, 58.19; H, 10.24: N, 5.65.

EXAMPLE 3

1,5(Nonylimino)-1,5-dideoxy-D-glucitol

A solution of 1,5-dideoxy-1,5-imino-D-glucitol (0.5 g, 0.0031 mole), nonyl aldehyde (0.52 g, 0.0037 mole) and 5% Pd black (0.1 g) in methanol (100 ml) was hydrogenated (60 psi/25° C./46 hrs.). After filtering the resulting mixture, the filtrate was concentrated with a gentle flow of nitrogen to an oily solid. This material was stirred with a small amount of acetone and the solid filtered by reduced pressure. Recrystallization from ethanol-acetone gave the title compound, DSC ca. 109° C. Structure assignment was supported by NMR, infrared spectra and elemental analysis (289.4).

Analysis calcd. for $C_{15}H_{31}NO_4$: C, 62.25; H, 10.80; N, 4.84. Found: C, 62.15; H, 10.86; N, 4.79.

Example 4

1,5-(Tetradecylimino)-1,5-dideoxy-D-glucitol

A solution of 1,5-dideoxy-1,5-imino-D-glucitol (1.0 g, 0.006 mole), tetradecyl aldehyde (1.48 g, 0.007 mole) and 5% Pd black (0.2 g) in methanol (40 ml) was hydrogenated (5 psi/25° C./64 hrs.). After filtering the resulting mixture, the filtrate was concentrated to a white solid with a gentle flow of nitrogen. The solid was purified by silica gel chromatography and recrystallized from methanol. Recrystallization from water-acetone gave the title compound, m.p. ca. 103° C. Structure assignment was supported by NMR, infrared spectra and mass spectroscopy.

EXAMPLE 5

The compounds prepared in Examples 1 to 4 were tested for inhibition of visna virus in vitro in a plaque reduction assay as follows:

METHOD

Cell and virus propagation

Sheep choroid plexus(SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at $-70°$ C.

Plaque reduction assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3–4 weeks. To terminate the test: cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 well plate assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 $\mu$l of virus added in M-199 supplemented with 2% lamb serum. After 1 hour, 75 $\mu$L of medium containing test compound was added to each well containing virus. After 2–3 weeks incubation the cytopathic effect of the virus was determined by staining with a vital stain. Cell viability was measured by determining stain density using a 96 well plate reader.

Control wells without virus were completed to determine the toxicity of compounds.

RESULTS

Table 1, below, sets forth the results of the assay for the compounds of Examples 1, 2, 3 and 4 compared to the N-butyl derivative of 1,5-dideoxy-1,5-imino-D-glucitol (N-Bu-DNJ) as a control standard.

TABLE 1

PLAQUE REDUCTION ASSAY

| Compound Example No. | Concentration | Toxicity | Antiviral Activity |
|---|---|---|---|
| 1 | — | — | — |
| 2 | 10 μM | 0 | 94% |
|   | 1 μM | 2 | 100% |
| 3 | 1 mM | 4 | 100% |
|   | 10 μM | 0 | 69% |
| 4 | 1 mM | 4 | 100% |
|   | 0.1 mM | 4 | 100% |
|   | 10 μM | 1 | 84% |
| N-Bu-DNJ | 1 mM | 0 | 100% |
|   | 10 μM | 0 | 57% |

Toxicity graded on 0 to 4 scale 0 = no toxicity, 4 = total cell lysates
N-Bu-DNJ = N-butyl-deoxynojirimycin used as a control standard.

EXAMPLE 6

The compounds prepared in Examples 1 to 4 were tested for inhibition of almond α-glucosidase and yeast α-glucosidase as follows:

ASSAYS FOR ALPHA-GLUCOSIDASE (YEAST) AND BETA-GLUCOSIDASE (ALMONDS)

Yeast alpha-glucosidase and almond beta-glucosidase activities were measured by a modification of the method of Evans, et al., *Phytochemistry* 22, 768–770 (1983). The modifications included 1) assay of activities at pH 7.4 in HEPES (N-2-hydroxyethylpiperazine-N'-2-ethanesulfonic acid) buffer, 2) measurement in 96 well microtiter plates and 3) inclusion of 10% DMSO in control and test samples.

The release of p-nitrophenol from the substrate p-nitrophenylglycoside was measured spectrophotometrically in the presence and absence of test compound. Each assay included a known inhibitor of the enzyme as a standard. $IC_{50}$ values were determined for compounds which inhibited the enzymes more than 50% at a 1 millimolar concentration.

ALPHA-GLUCOSIDASE INHIBITION ASSAY, pH 7.4

To 100 μl 50 mM HEPES buffer, pH 7.4, in a microtiter plate, add 20 μl test compound in DMSO (DMSO alone in control), 40 μl (0.013 units) yeast alpha-glucosidase (Sigma) in HEPES buffer and pre-incubate at room temperature for 15 minutes. Add 40 μl 1.25 mM p-nitrophenyl-alpha-D-glucopyranoside (Sigma) in HEPES buffer, as substrate, and monitor absorbance change at 405 nm in Biotek EIA Auto-reader. Absorption change was measured at 15 to 25 minutes (reaction was linear for at least 30 minutes). Each sample was tested in triplicate. $IC_{50}$ values were determined from the linear portion of the log concentration vs % inhibition curve obtained from a minimum of 3 points. Deoxynojirimycin was used as standard inhibitor.

BETA-GLUCOSIDASE INHIBITION ASSAY pH 7.4:

To 100 μl 50 mM HEPES buffer, pH 7.4, in a microtiter plate, add 20 μl test compound in DMSO (DMSO alone in control), 40 μl (0.136 units) beta-glucosidase (Sigma) in HEPES buffer and pre-incubate at room temperature for 15 minutes. Add 40 μl 1.25 mM p-nitrophenyl-beta-D-glucopyranoside in HEPES buffer, as substrate and monitor absorbance change at 405 nm in a Biotek EIA Autoreader. Absorption change was measured at 15 to 25 minutes (reaction is linear for at least 30 minutes). Each sample was tested in triplicate. $IC_{50}$ values were determined from the linear portion of the log concentration vs % inhibition curve obtained from a minimum of 3 points. Castanospermine was used as standard inhibitor.

pH 4.8:

To 100 μl 50 mM sodium citrate buffer, pH 4.8, in a microtiter plate, add 15 μl test compound in DMSO (DMSO alone in control), 20 μl (0.017 units) beta-glucosidase (Sigma) in citrate buffer and pre-incubate at room temperature for 15 minutes. Add 25 μl 2.50 mM p-nitrophenyl-beta-D-glucopyranside in citrate buffer, as substrate. Incubate at room temperature 20 minutes (reaction is linear for at least 30 minutes). Add 50 μl 0.4M NaOH. Read absorption change at 405 nm in a Biotek EIA Autoreader. Each sample was tested in triplicate. $IC_{50}$ values were determined from the linear portion of the log concentration vs % inhibition curve obtained from a minimum of 3 points. Castanospermine was used as standard inhibitor.

RESULTS

Table 2, below, sets forth the results of the enzyme inhibition assay for the compounds of Examples 1, 2, 3 and 4 compared to the lower N-alkyl derivatives of 1,5-dideoxy-1,5-imino-D-glucitol (N-alkyl-DNJ), namely the methyl-, ethyl-, and butyl-DNJ compounds.

TABLE 2

| N-alkyl-DNJ Compound Tested | Enzyme Inhibition-$IC_{50}$ | | | Inhibition Index | |
|---|---|---|---|---|---|
| | Almond β-Glucosidase pH 7.4 | β-Glucosidase pH 4.8 | Yeast α-Glucosidase pH 7.4 | β-Glucosidase ratio: pH 4.8 / pH 7.4 | at pH 7.4 ratio: α-Glucosidase / β-Glucosidase |
| Methyl | 102 μM | 366 μM | 54 μM | 3.5 | 0.53 |
| Ethyl | 67% at 1 mM | ~1 mM | 51% at 1 mM | ~1 | ~1 |
| Butyl | 155 μM | 47% at 1 mM | 536 μM | 6.45 | 3.45 |
| Pentyl-Ex. 1 | 15 μM | 423 μM | 444 μM | 28.2 | 29.5 |
| Hexyl-Ex. 2 | 4.8 μM | 144 μM | 371 μM | 30 | 77.3 |
| Nonyl-Ex. 3 | 18 μM | 196 μM | 267 μM | 10.8 | 14.8 |
| Tetradecyl-Ex. 4 | 31% at 10 μM | 22% at 10 μM | 0% at 10 μM | — | — |

The foregoing results demonstrate the advantageous properties of the N-pentyl-, N-hexyl-, and N-nonyl derivatives of DNJ compared to the lower N-alkyl derivatives as well as the long chain N-tetradecyl derivative.

EXAMPLE 7

The N-hexyl-DNJ and N-nonyl-DNJ of Examples 2 and 3, respectively, were demonstrated to inhibit HIV-1 in the following tests which measured reduction of cytopathogenic effect in virus-infected syncytium-sensitive Leu-3a-positive CEM cells grown in tissue culture.

Tissue culture plates were incubated at 37° C. in a humidified, 5% $CO_2$ atmosphere and observed microscopically for toxicity and/or cytopathogenic effect (CPE). At 2 and 6 days after infection, fresh dilutions of each test article were prepared from the frozen stock, and a 20 μl volume of each dilution (prepared as a 10× concentration was added to the appropriate wells of both infected and uninfected cells.

On the 9th day post-infection, the cells in each well were resuspended and a 100 μl sample of each cell suspension was removed for use in an MTT assay. A 20 μl volume of a 5 mg/ml solution of 3-(4,5-dimethylthiazol-2-yl)-2,5-diphenyltetrazolium bromide (MTT) was added to each 100 μl cell suspension, and the cells were incubated at 37° C. in 5% $CO_2$ for 4 hours. During this incubation MTT is metabolically reduced by living cells, resulting in the production of a colored formazan product. A 100 μl volume of a solution of 10% sodium dodecyl sulfate in 0.01N hydrochloric acid wa added to each sample, and the samples were incubated overnight. The absorbance at 590 nm was determined for each sample using a Molecular Devices $V_{max}$ microplate reader. This assay detects drug-induced suppression of viral CPE, as well as drug cytotoxicity, by measuring the generation of MTT-formazan by surviving cells.

Assays were done in 96-well tissue culture plates. CEM cells were treated with polybrene at a concentration of 2 μg/ml, and an 80 μl volume of cells ($1 \times 10^4$ cells) was dispensed into each well. A 100 μl volume of each test article dilution (prepared as a 2× concentration) was added to 5 wells of cells, and the cells were incubated at 37° C. for 1 hour. A frozen culture of HIV-1, strain HTLV-III$_B$, was diluted in culture medium to a concentration of $5 \times 10^4$ TCID$_{50}$ per ml, and a 20 μl volume (containing $10^3$ TCID$_{50}$ of virus) was added to 3 of the wells for each test article concentration. This resulted in a multiplicity of infection of 0.1 for the HIV-1 infected samples. A 20 μl volume of normal culture medium was added to the remaining wells to allow evaluation of cytotoxicity. Each plate contained 6 wells of untreated, uninfected, cell control samples and 6 wells of untreated, infected, virus control samples. Dideoxycytidine (DDC) and dideoxyadenosine (DDA) were included as positive control compounds.

Table 3, below, sets forth the results of the foregoing antiviral testing of the N-hexyl-DNJ and N-nonyl-DNJ compared to the N-butyl-DNJ. These results demonstrate the advantageous reduction in ID$_{50}$ (median inhibitory dose) of the N-hexyl-DNJ and N-nonyl-DNJ compared to the N-butyl-DNJ.

TABLE 3
ANTIVIRAL EVALUATION

| Compound | Percent Reduction of CPE[a] | | | | | | ID$_{50}$ (μg/ml) |
|---|---|---|---|---|---|---|---|
|  | 500 μg/ml | 100 μl/ml | 32 μg/ml | 10 μg/ml | 3.2 μg/ml | 1.0 μg/ml |  |
| N-Butyl-DNJ[b] | 50.7 | 53.3 | 49.8 | 42.6 | — | — | 34 |
| N-nonyl-DNJ | T | T | 28.9 | 62.5 | 25.7 | 0 | 6.9 |
| N-hexyl-DNJ[b] | 146.9 | 65.1 | 68.0 | 65.6 | 15.6 | 0 | 7.3 |
| Compound | 50 μg/ml | 10 μg/ml | 3.2 μg/ml | 1.0 μg/ml |  |  | ID$_{50}$ (μg/ml) |
| DDI | T | 75.6 | 49.6 | 28.3 |  |  | 3.0 |
| Compound | 5.0 μg/ml | 1.0 μg/ml | 0.32 μg/ml | 0.1 μg/ml | 0.032 μg/ml | 0.01 μg/ml | ID$_{50}$ (μg/ml) |
| DDC | T | T | T | T | 73.9 | 41.5 | 0.01 |

[a]The percent reduction of viral CPE was calculated by the formula:

$$\left[ \frac{\left(\begin{array}{c}\text{Absorbance of drug-treated,} \\ \text{infected sample}\end{array}\right) - \left(\begin{array}{c}\text{Absorbance of} \\ \text{virus control}\end{array}\right)}{(\text{Absorbance of cell control}) - (\text{Absorbance of virus control})} \right] \times 100.$$

[b]Solubility problem; compound did not completely dissolve in the aqueous solvent.
T = Toxic The antiviral agents described herein can be used for administration to patients infected with the human immunodeficiency virus by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such further examples be included within the scope of the appended claims.

What is claimed is:

1. The method of inhibiting lentivirus in a warm blooded mammal which comprises treating said mammal with a lentivirally inhibitory effective amount of 1,5-(hexylimino)-1,5-dideoxy-D-glucitol or a pharmaceutically acceptable salt thereof.

2. The method of inhibiting lentivirus in a warm blooded mammal which comprises treating said mammal with a lentivirally inhibitory effective amount of 1,5-(nonylimino)-1,5-dideoxy-D-glucitol or a pharmaceutically acceptable salt thereof.

* * * * *

UNITED STATES PATENT AND TRADEMARK OFFICE
CERTIFICATE OF CORRECTION

PATENT NO. : 5,030,638

DATED : July 9, 1991

INVENTOR(S) : RICHARD A. PARTIS AND RICHARD A. MUELLER

It is certified that error appears in the above-identified patent and that said Letters Patent is hereby corrected as shown below:

Column 1, line 24, "$T4^{30}$" should read --$T4^+$-- and "$CD4^{30}$" should read --$CD4^+$--. Column 1, line 37, after "As used herein" insert --HIV is meant to refer to--. Column 2, line 2, after "(1987)"; insert --and Gruters et al., Nature 330, 74-77 (1987).-- Column 2, line 45, "o-glucosidase" should read --$\alpha$-glucosidase--.

Signed and Sealed this

Twenty-third Day of February, 1993

Attest:

STEPHEN G. KUNIN

Attesting Officer

Acting Commissioner of Patents and Trademarks